(12) United States Patent
Manzo

(10) Patent No.: US 7,520,883 B2
(45) Date of Patent: Apr. 21, 2009

(54) METHOD AND APPARATUS FOR ANASTOMOSIS INCLUDING AN ANCHORING SLEEVE

(75) Inventor: Scott Manzo, Shelton, CT (US)

(73) Assignee: Tyco Healthcare Group LP, Norwalk, CT (US)

( * ) Notice: Subject to any disclaimer, the term of this patent is extended or adjusted under 35 U.S.C. 154(b) by 439 days.

(21) Appl. No.: 10/514,774

(22) PCT Filed: Apr. 16, 2003

(86) PCT No.: PCT/US03/11692

§ 371 (c)(1),
(2), (4) Date: Nov. 17, 2004

(87) PCT Pub. No.: WO04/000136

PCT Pub. Date: Dec. 31, 2003

(65) Prior Publication Data

US 2005/0182427 A1 Aug. 18, 2005

Related U.S. Application Data

(60) Provisional application No. 60/390,782, filed on Jun. 20, 2002.

(51) Int. Cl.
*A61B 17/08* (2006.01)
*A61B 17/10* (2006.01)

(52) U.S. Cl. ..................... 606/153; 606/139

(58) Field of Classification Search .............. 606/139, 606/142, 144, 148, 153, 198, 230, 186; 227/66, 227/67, 175.1, 179.1
See application file for complete search history.

(56) References Cited

U.S. PATENT DOCUMENTS

| 2,127,903 | A | | 8/1938 | Bowen |
| 3,626,948 | A | * | 12/1971 | Glick et al. ............ 606/230 |
| 4,553,543 | A | | 11/1985 | Amarasinghe |
| 4,803,984 | A | | 2/1989 | Narayanan et al. |
| 4,848,367 | A | | 7/1989 | Avant et al. |
| 4,911,164 | A | | 3/1990 | Roth |

(Continued)

FOREIGN PATENT DOCUMENTS

WO    WO03/088848    10/2003

(Continued)

OTHER PUBLICATIONS

U.S. Appl. No. 10/516,437, entitled "Method and Apparatus for Anastomosis Including Annular Joining Member", filed Nov. 30, 2004.

(Continued)

*Primary Examiner*—Julian W Woo

(57) ABSTRACT

Apparatus for performing a surgical anastomosis are disclosed. The apparatus include a tubular body having a proximal end and a distal end, an onion sleeve portion formed near the distal end of the tubular body and an inner tube disposed within the tubular body. The inner tube includes at least one pair of longitudinally aligned needle passages formed below the onion sleeve portion of the tubular body. The apparatus further includes at least one needle assembly disposed within the at least one pair of longitudinally aligned needle passages and a firing assembly operatively coupled to the proximal end of the tubular body. The firing assembly is configured and adapted to eject the pair of needles from the apparatus.

14 Claims, 12 Drawing Sheets

U.S. PATENT DOCUMENTS

| | | | |
|---|---|---|---|
| 4,957,499 A | | 9/1990 | Lipatov et al. |
| 5,047,039 A | | 9/1991 | Avant et al. |
| 5,122,156 A | | 6/1992 | Granger et al. |
| 5,234,448 A | | 8/1993 | Wholey et al. |
| 5,403,333 A | | 4/1995 | Kaster et al. |
| 5,411,508 A | | 5/1995 | Bessler et al. |
| 5,425,739 A | | 6/1995 | Jessen |
| 5,464,414 A | | 11/1995 | Cziffer |
| 5,464,415 A | | 11/1995 | Chen |
| 5,478,353 A | | 12/1995 | Yoon |
| 5,486,187 A | | 1/1996 | Schenck |
| 5,496,332 A | * | 3/1996 | Sierra et al. ................ 606/139 |
| 5,540,701 A | | 7/1996 | Sharkey et al. |
| 5,545,171 A | | 8/1996 | Sharkey et al. |
| 5,549,619 A | | 8/1996 | Peters et al. |
| 5,554,162 A | | 9/1996 | DeLange |
| 5,569,272 A | | 10/1996 | Reed et al. |
| 5,578,044 A | | 11/1996 | Gordon et al. |
| 5,591,179 A | | 1/1997 | Edelstein |
| 5,591,206 A | | 1/1997 | Moufarrèege |
| 5,695,504 A | | 12/1997 | Gifford, III et al. |
| 5,700,272 A | | 12/1997 | Gordon et al. |
| 5,700,273 A | * | 12/1997 | Buelna et al. ................ 606/148 |
| 5,702,412 A | | 12/1997 | Popov et al. |
| 5,707,380 A | | 1/1998 | Hinchliffe et al. |
| 5,713,889 A | | 2/1998 | Chang |
| 5,716,370 A | | 2/1998 | Williamson, IV et al. |
| 5,741,277 A | | 4/1998 | Gordon et al. |
| 5,797,934 A | | 8/1998 | Rygaard |
| 5,814,005 A | | 9/1998 | Barra et al. |
| 5,817,113 A | | 10/1998 | Gifford, III et al. |
| 5,830,125 A | * | 11/1998 | Scribner et al. ............. 606/139 |
| 5,833,698 A | | 11/1998 | Hinchliffe et al. |
| 5,868,762 A | | 2/1999 | Cragg et al. |
| 5,904,697 A | | 5/1999 | Gifford, III et al. |
| 5,944,730 A | | 8/1999 | Nobles et al. |
| 5,951,576 A | | 9/1999 | Wakabayashi |
| 5,980,483 A | | 11/1999 | Dimitri |
| 6,024,748 A | | 2/2000 | Manzo et al. |
| 6,048,351 A | | 4/2000 | Gordon et al. |
| 6,051,007 A | | 4/2000 | Hogendijk et al. |
| 6,063,114 A | | 5/2000 | Nash et al. |
| 6,080,167 A | | 6/2000 | Lyell |
| 6,096,051 A | | 8/2000 | Kortenbach et al. |
| 6,117,144 A | * | 9/2000 | Nobles et al. ................ 606/144 |
| 6,149,658 A | | 11/2000 | Gardiner et al. |
| 6,152,937 A | | 11/2000 | Peterson et al. |
| 6,171,319 B1 | | 1/2001 | Nobles et al. |
| 6,171,321 B1 | | 1/2001 | Gifford, III et al. |
| 6,176,864 B1 | | 1/2001 | Chapman |
| 6,203,553 B1 | | 3/2001 | Robertson et al. |
| 6,241,742 B1 | | 6/2001 | Spence et al. |
| 6,254,617 B1 | | 7/2001 | Spence et al. |
| 6,280,460 B1 | | 8/2001 | Bolduc et al. |

FOREIGN PATENT DOCUMENTS

| | | |
|---|---|---|
| WO | WO2004/000093 | 12/2003 |
| WO | WO2004/000134 | 12/2003 |
| WO | WO2004/000135 | 12/2003 |
| WO | WO2004/000136 | 12/2003 |
| WO | WO2004/098148 | 11/2004 |

OTHER PUBLICATIONS

U.S. Appl. No. 10/517,404, entitled "Method and Apparatus for Anastomosis Including an Anchoring Sleeve", filed Dec. 7, 2004.

U.S. Appl. No. 10/518,040, entitled "Method and Apparatus for Anastomosis Including Annular Adjoining Member", filed Dec. 9, 2004.

U.S. Appl. No. 10/514,140, entitled Method and Apparatus for Radical Prostatectomy Anastomosis, filed Nov. 9, 2004.

U.S. Appl. No. 10/516,434, entitled "Method and Apparatus for Anastomosis", filed Nov. 30, 2004.

* cited by examiner

METHOD AND APPARATUS FOR ANASTOMOSIS INCLUDING AN ANCHORING SLEEVE

CROSS REFERENCE TO RELATED APPLICATIONS

This is a National Stage Application of PCT/US 03/11692 under 35 USC §371 (a), which claims priority of U.S. Provisional Patent Application Ser. No. 60/390,782 filed Jun. 20, 2002, now abandoned, the entire contents of which are hereby incorporated by reference.

BACKGROUND

1. Technical Field

The present disclosure relates to apparatus and methods for anastomosing two hollow body parts and, more particularly apparatus and methods for anastomosing a urethral stump of a patient to the bladder following a radical prostatectomy.

2. Background of Related Art

Anastomosis is the bringing together and/or joining of hollow or tubular structures. Most body conduits are generally cylindrical in configuration and have a circular cross-section. When it is desired to suture such a conduit, typically for attachment to another body conduit, sutures are placed around the circumference of the conduit in order to maintain the patency of its lumen or channel. This type of attachment is commonly referred to as an anastomosis. It can be appreciated that the sutures made on top of the conduit (i.e., on the side facing the surgeon) in an anastomosis are made relatively more easily than the sutures made underneath the conduit (i.e., on the side facing away from the surgeon).

The complexity of anastomosis attachment is made manifestly apparent in a surgical procedure referred to generally as a radical prostatectomy (i.e., a well established surgical procedure for patients with localized prostatic carcinoma). In general, radical prostatectomy procedures require the removal of cancerous tissue while preserving sexual function and continence in the patient. There are two primary types of radical prostatectomy approaches for the removal of prostate cancer, the retropubic approach and the perineal approach.

In the retropubic approach, a long up-and-down incision is made in the midline of the abdomen from the navel to the pubic bone. After the lymph nodes have been removed for study by the pathologist and a determination has been made to proceed with the removal of the prostate gland, the space underneath the pubic bone is cleaned and dissected and the removal of the entire prostate gland is generally begun at the end that is farthest from the bladder, i.e., next to the external urethral sphincter. Next, the prostatic urethra is divided, the prostatic urethra and the prostate gland through which it goes are then pulled upwards toward the bladder while the dissection continues behind the prostate gland, separating it from the layer of tissue that is connected to the rectum on its other side. As the dissection continues between the prostate and the rectum, the seminal vesicles, which are behind the base of the bladder will be removed along with the prostate gland. Once the seminal vesicles are free, the entire prostate gland and the seminal vesicles are removed. The bladder neck is then stitched closed to a small enough diameter so that it is about the same size as the stump of the urethra from which the prostate was detached. The bladder neck is then pulled down into the pelvis and positioned against the urethral stump and stitched thereto. This stitching is done typically around a Foley catheter which has been inserted through the penis all the way into the bladder.

In the perineal approach, an inverted "U" shaped incision is made going right over the anus, with the center of the "U" about three centimeters above the margin of the anus. The prostate gland is then freed from its surrounding structures by gentle dissection, and the urethra at the end of the prostate farthest from the bladder is isolated and divided. The bladder neck is freed from the prostate, and, once the prostate gland has been removed and the bladder neck has been closed sufficiently so that the size of its opening approximates the size of the urethral opening, the urethra and the bladder neck are stitched together. Once again, a Foley catheter is left in place postoperatively for about two weeks.

In each of the above described procedures, it is the attachment of the urethral stump to the bladder neck which is particularly difficult and complex. This difficulty is complicated by the tendency of the urethral stump to retract into adjacent tissue. As a result, considerable time and effort must be expended to re-expose the urethral stump and begin the re-anastomosis procedure. Further complicating this procedure is the fact that the urethral stump is hidden beneath the pubic bone thus requiring that the surgeon work at a difficult angle and in positions that are uncomfortable and limiting.

Various devices have been proposed for facilitating this procedure. In U.S. Pat. No. 5,591,179 issued to Edelstein there is disclosed a suturing device including a shaft with portions defining an interior channel extending between a proximal and a distal end of the shaft. This channel includes a generally axial lumen which extends to the proximal end of the shaft and a generally transverse lumen which extends from the axial lumen distally outwardly to an exit hole at the outer surface of the shaft. A needle and suture can be back loaded into the transverse lumen of the channel while a generally non-compressible member can be movably mounted in the axial lumen of the channel. At the proximal end of the shaft a handle is provided with means operative to push the member distally through the lumen to deploy or expel the needle.

In U.S. Pat. No. 4,911,164 issued to Roth there is disclosed a suture guide with a curved distal portion. The distal portion of the suture guide has a plurality of exterior axial grooves which can be used to align and guide a curved needle and attached suture. In order to drive the urethral stump to an accessible position, the device is provided with a plurality of outwardly extendable members which engage the lumen of the urethra. These members make it possible to push the urethral stump into approximation with the bladder neck.

In U.S. Pat. No. 5,047,039 issued to Avant et al. there is disclosed a surgical device for the ligation of a dorsal vein and subsequent anastomosis. This device contains a pair of enclosed needles each having an attached suture which needles may be driven from the shaft of the device into adjacent tissue.

In general, none of the devices disclosed in the prior art references above is simple to use or makes the anastomosis of the urethral stump to the bladder neck easier. As such, each surgical procedure using prior art devices continues to be time consuming and requires great skill in order to be performed. In addition, these prior art references do not disclose a suture device which can accurately position a plurality of anchor and suture combinations, for use at or near the severed end of a body conduit, simultaneously. Accordingly, the need exists for radical prostatectomy anastomosis devices which overcome the drawbacks of the prior art devices and which are quick and simple to use.

SUMMARY OF THE INVENTION

Apparatus and methods for performing a surgical anastomotic procedure are disclosed herein. The apparatus according to the present disclosure includes a tubular body having a proximal end and a distal end and an onion portion formed near the distal end of the tubular body for engaging a first body vessel. The onion portion has a first position and a second position outside the radial dimension of the tubular body. The apparatus has an inner tube disposed within the tubular body and slidably movable to deploy the onion portion from the first position to the second position. The inner tube has a plurality of passages. The apparatus has a plurality of needles, each needle being disposed in one of the passages. The apparatus has a firing assembly for deploying the needles from the passages.

The tubular body may have a first position in which the onion sleeve portion is substantially co-planar with the tubular body and a second position in which the onion sleeve portion is deployed transversely with respect to the tubular body.

The inner tube may be slidably movable from a first position in which the onion sleeve portion is in the first position and a second position in which the onion sleeve is in the second position. The passages may comprise a pair of passages formed below the onion sleeve portion of the tubular body, including a distal passage and a proximal passage. Preferably, the pair of passages are oriented toward one another.

The needles may comprise at least one needle assembly disposed within the pair of passages. Each needle assembly includes a pair of needles interconnected by a suture. A first needle of the pair of needles is desirably disposed within the distal passage and a second needle of the pair of needles is desirably disposed within the proximal passage.

The firing assembly desirably includes a plurality of rods, each of the rods being operatively coupled to at least one of the needles. The firing assembly may include a first needle driver knob and a second needle drive knob. The first needle driver knob is operatively coupled to at least one first rod with the at least one first rod desirably coupled with the first needle of the pair of needles. Preferably, distal advancement of the first rod causes the first needle of the pair of needles to be ejected from the apparatus. Preferably, proximal advancement of the second rod causes the second needle of the pair of needles to be ejected from the apparatus.

A preferred method for joining a first body vessel and a second body vessel comprises passing an apparatus through the second body vessel, the apparatus having an onion portion, so that the onion portion is received in the first body vessel. The first body vessel and second body vessel are approximated and joined, including deploying the onion portion so that the onion portion moves to a position outside the radial dimension of a tubular body of the apparatus and deploying at least one needle into at least one of the first body vessel and the second body vessel. The apparatus may have an inner tube with at least one pair of passages including a first passage and a second passage. The apparatus further includes at least one needle assembly disposed within the passages with each needle assembly including a pair of needles interconnected by a suture. Preferably, a first needle of the pair of needles in disposed within the first passage and a second needle of the pair of needles is disposed within the second passage.

These and other advantages and features of apparatus and methods disclosed herein, will become apparent through reference to the following description of embodiments, the accompanying drawings and the claims.

BRIEF DESCRIPTION OF THE DRAWINGS

The accompanying drawings, which are incorporated in and constitute a part of this specification, illustrate embodiments of the disclosure and, together with the general description given above, and the detailed description of the embodiments given below, serve to explain the principles of the present disclosure.

DETAILED DESCRIPTION OF PREFERRED EMBODIMENTS

Figure 1:
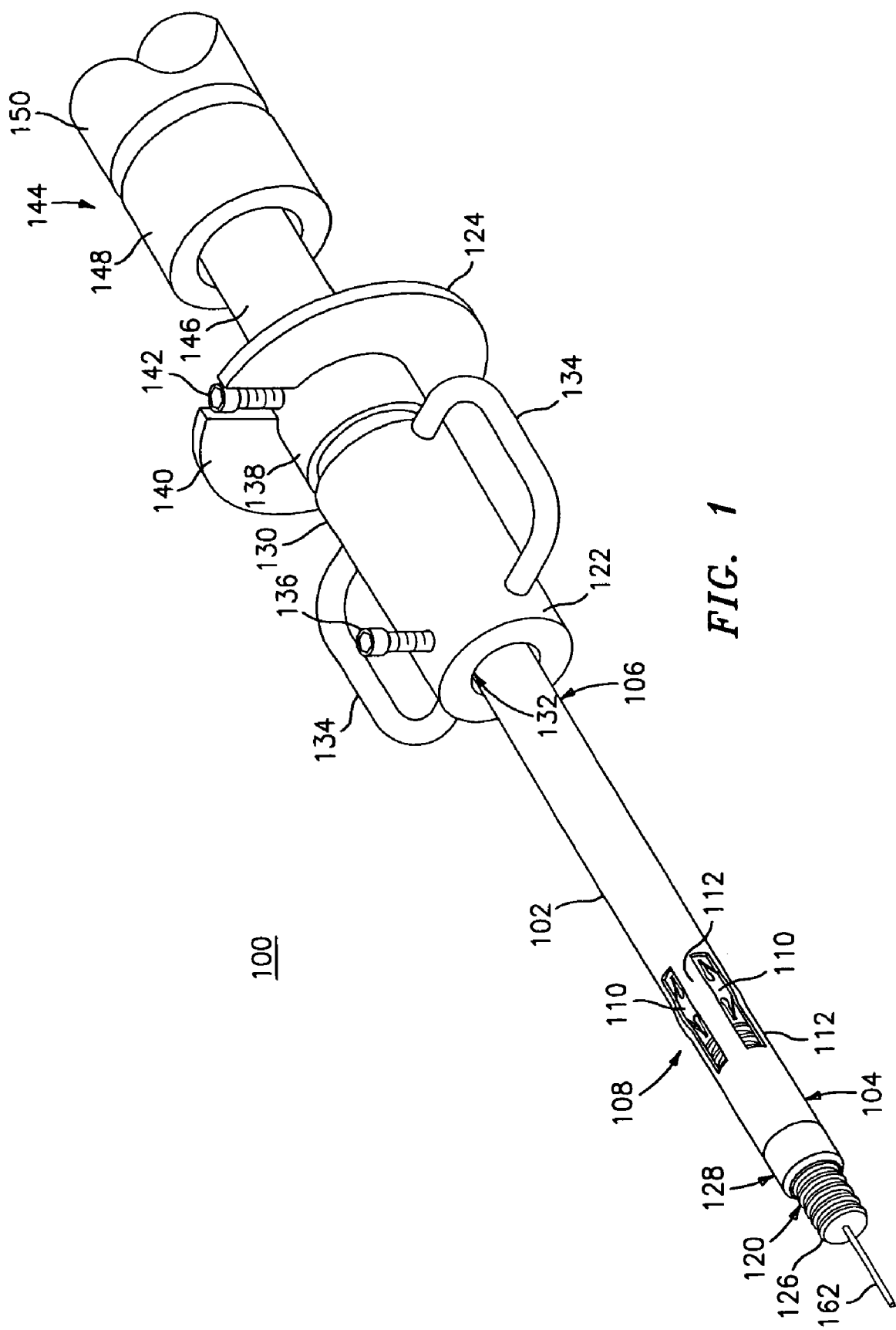
FIG. 1 is a perspective view of an anastomosis apparatus constructed in accordance with the present disclosure, while in a retracted position, as seen from a distal end thereof.
Figure 1A:
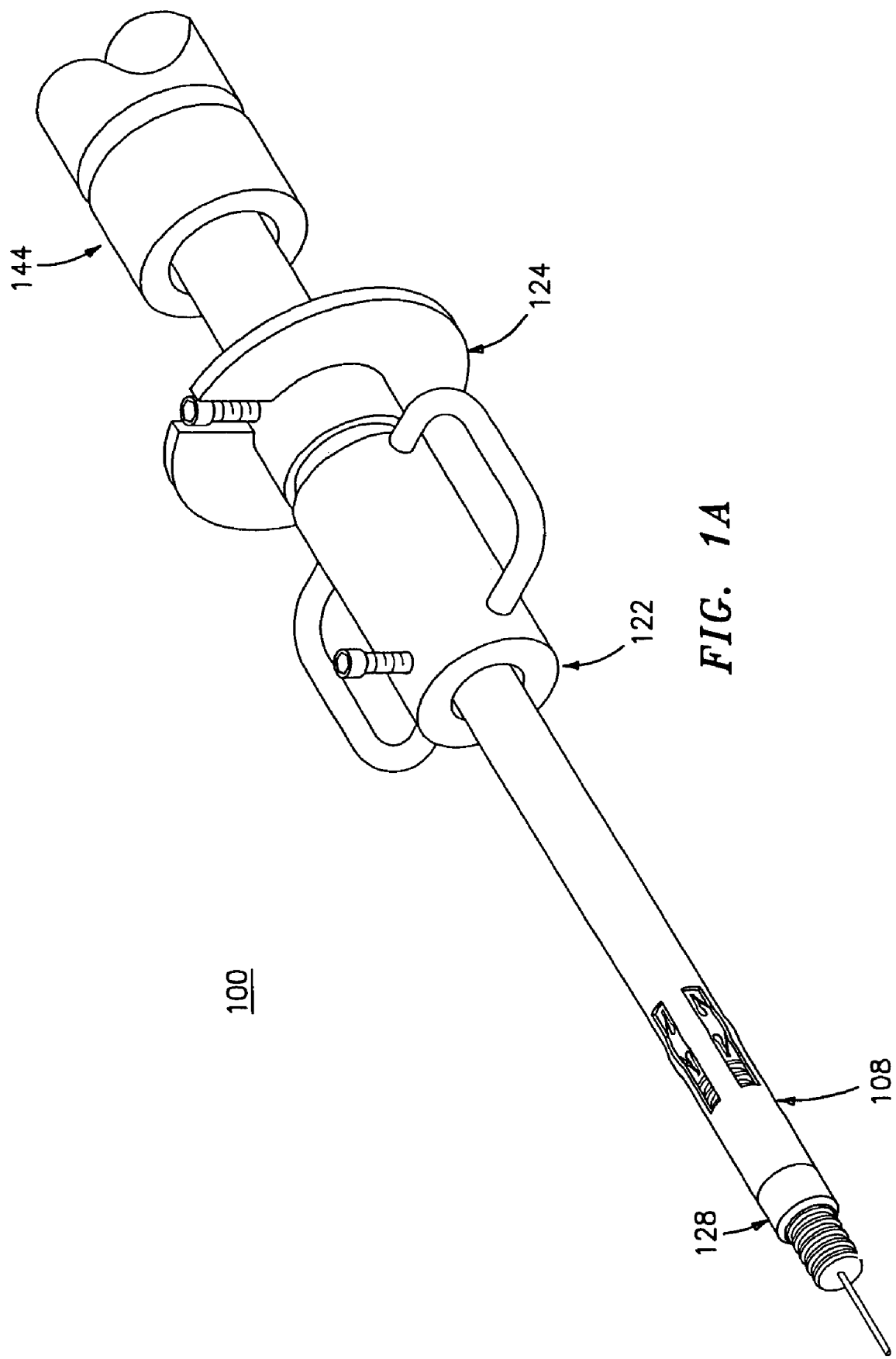
FIG. 1A is a perspective view of an engineering model of the anastomosis apparatus of FIG. 1, while in a retracted position.

Preferred embodiments of the presently disclosed anastomosis apparatus will now be described in detail with reference to the drawing figures wherein like reference numerals identify similar or identical elements. In the drawings and in the description which follows, the term "proximal", as is traditional will refer to the end of the surgical device or instrument of the present disclosure which is closest to the operator, while the term "distal" will refer to the end of the device or instrument which is furthest from the operator.

Referring now to FIGS. 1-10, an anastomosis apparatus, in accordance with the principles of the present disclosure, is shown generally as reference numeral 100. Although apparatus 100 offers significant advantages to a radical prostatectomy procedure, it will be understood that the device is applicable for use in any anastomotic procedure where two body conduits are to be joined, such as where the end of a conduit is to be sutured to a hollow body organ.

As seen in FIG. 1, apparatus 100 includes a tubular body 102 having a distal end 104 and a proximal end 106. Tubular body 102 includes an onion sleeve portion 108 formed near distal end 104. Preferably, onion sleeve portion 108 includes a plurality of longitudinally aligned slots 110 formed therein. Slots 110 define a plurality of longitudinal ribs 112 each having a number of transverse folding lines 114 formed along the length thereof. Preferably, as seen in detail in FIG. 3, each rib 112 includes a pair of fold lines 114A formed along the inner surface thereof and a fold line 114B, located between fold lines 114A, formed along the outer surface of rib 112.

Figure 1B:
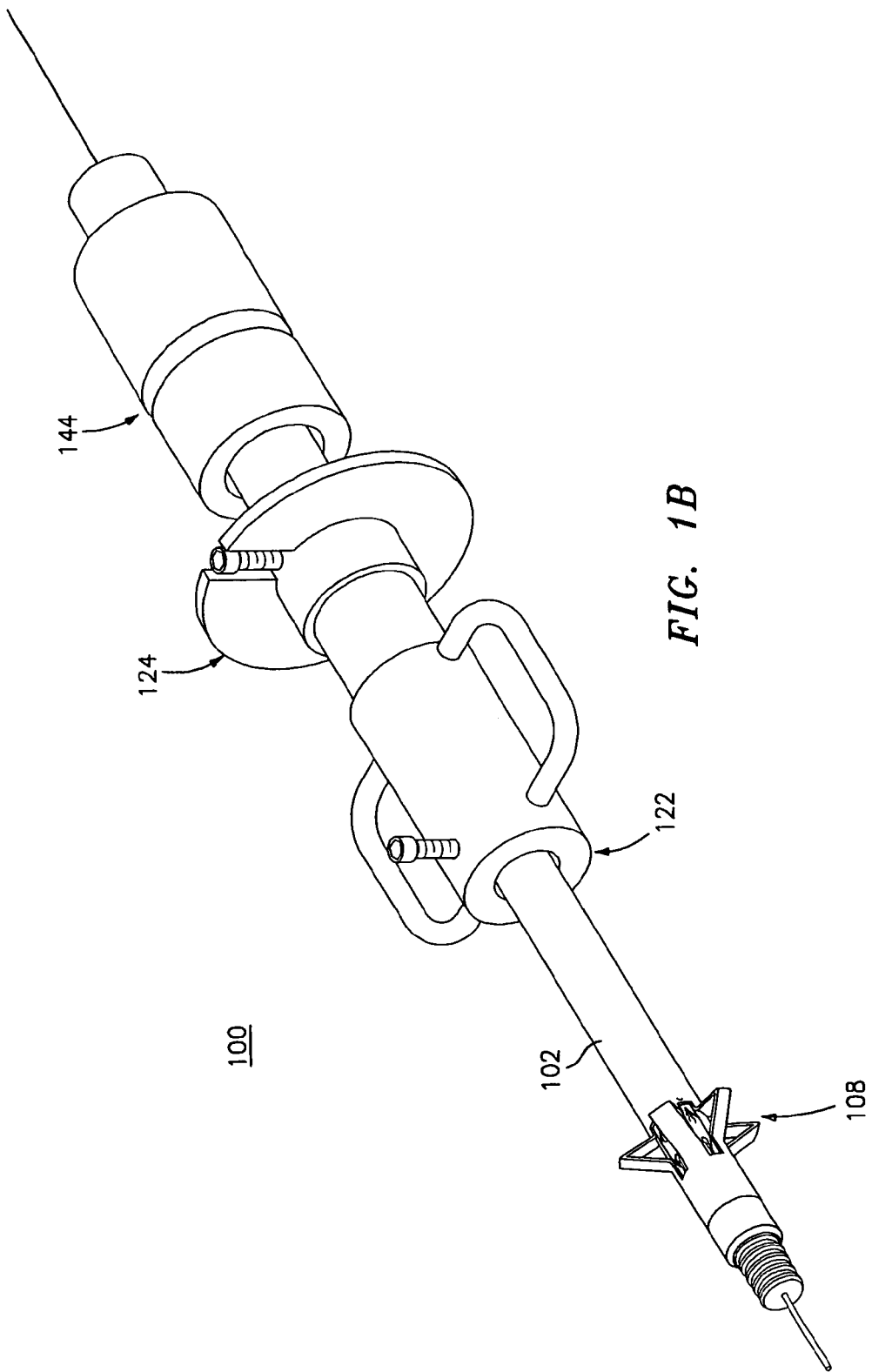
FIG. 1B is a perspective view of an engineering model of the anastomosis apparatus of FIG. 1, while in a deployed position.
Figure 2:
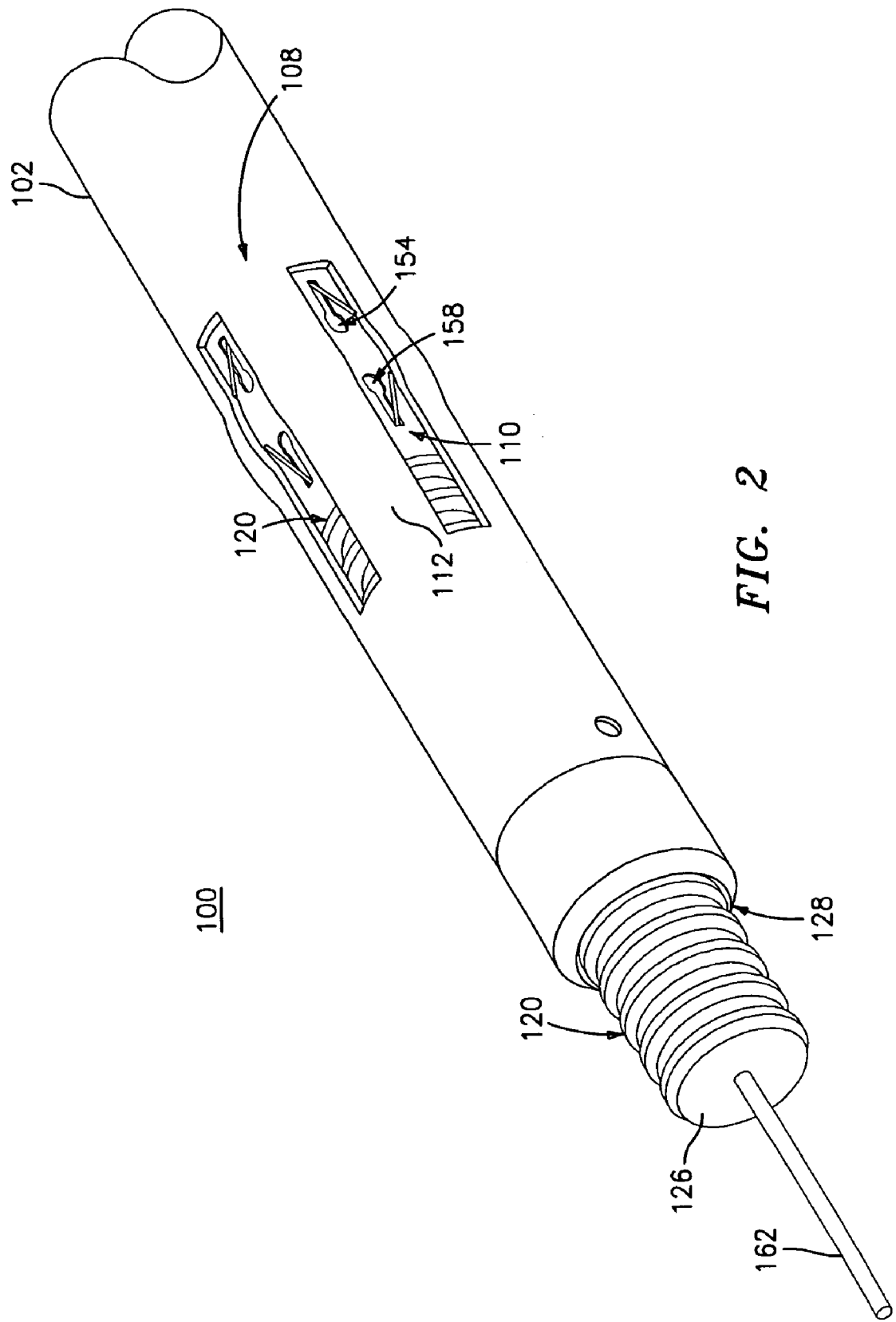
FIG. 2 is an enlarged perspective view of a distal end of the apparatus of FIG. 1, illustrating a radially deformable onion sleeve in a retracted configuration.
Figure 2A:
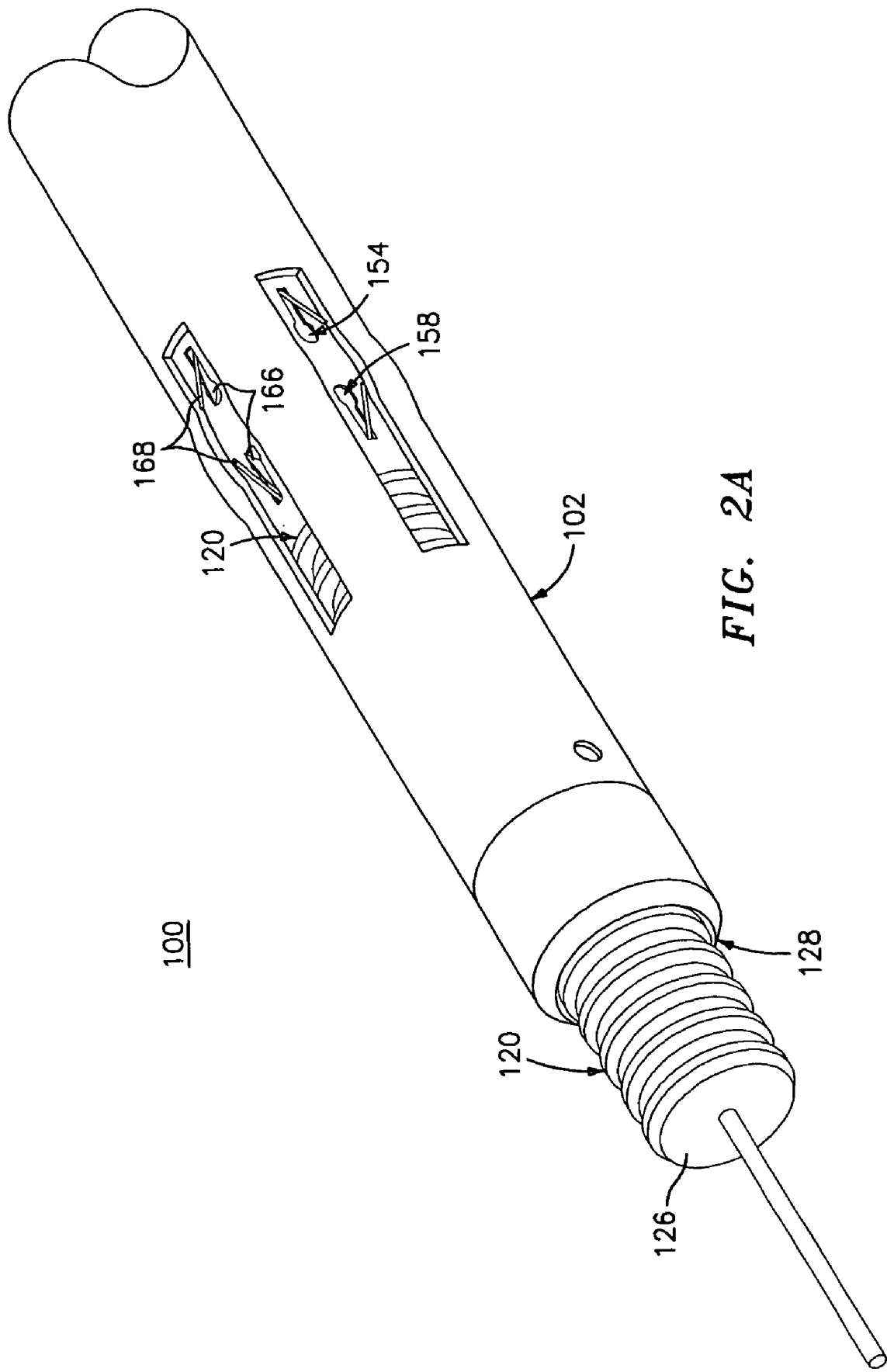
FIG. 2A is an enlarged perspective view of an engineering model of the anastomosis apparatus of FIG. 2.
Figure 3:
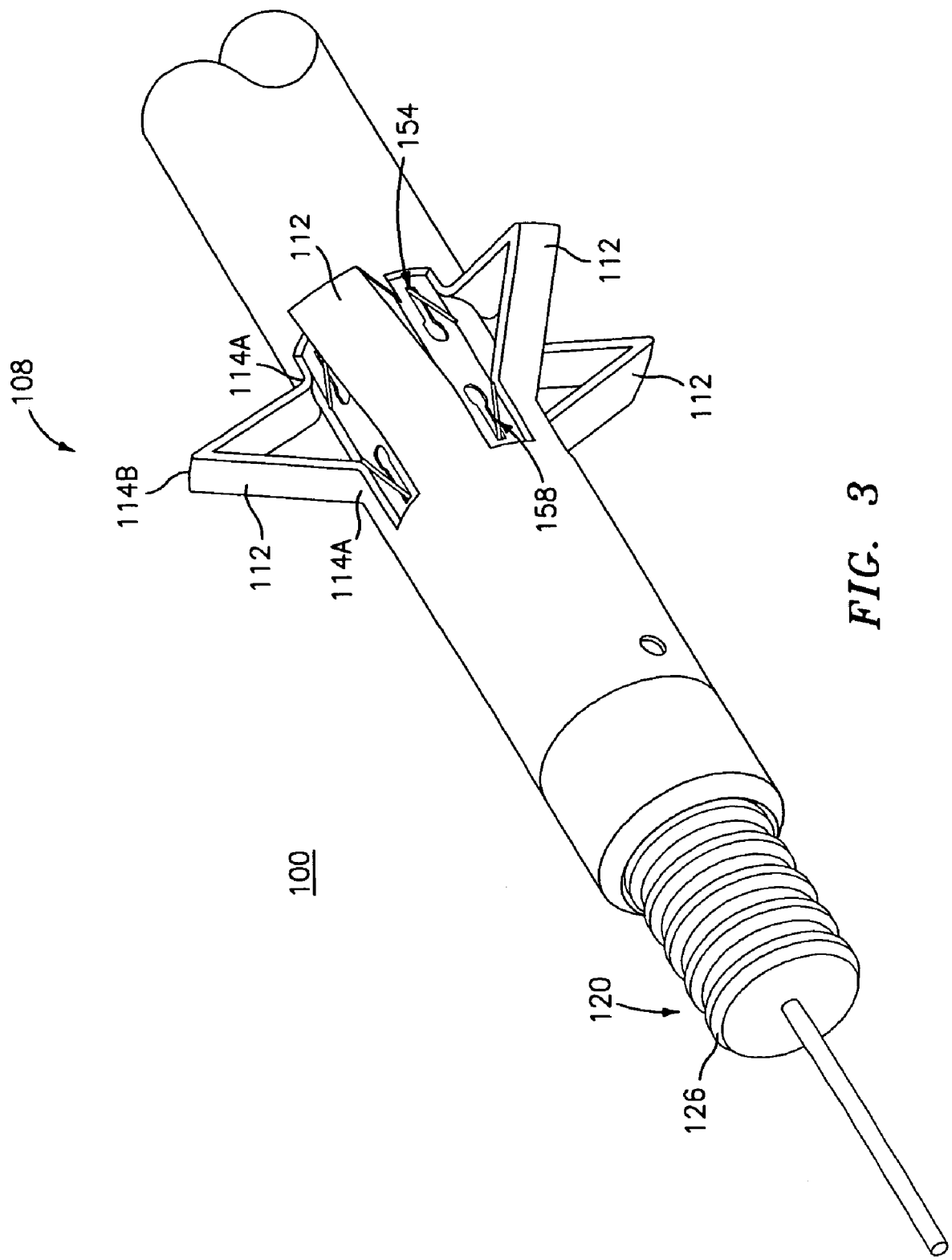
FIG. 3 is an enlarged perspective view of the distal end of the apparatus of FIG. 1, illustrating the radially deformable onion sleeve in a deployed configuration.
Figure 3A:
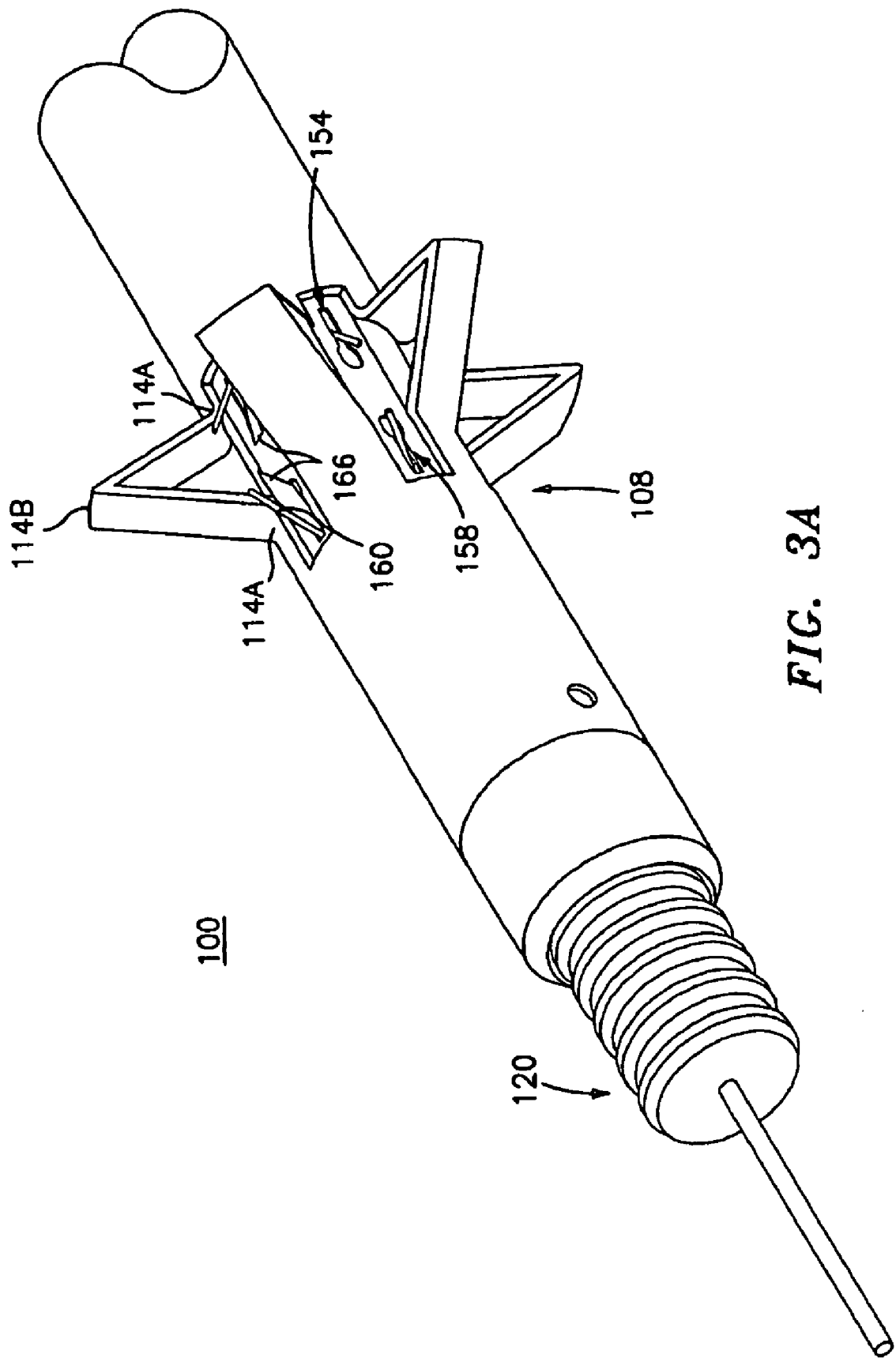
FIG. 3A is an enlarged perspective view of an engineering model of the anastomosis apparatus of FIG. 3.

In accordance with the present disclosure, tubular body 102 is movable from a first insertion/withdrawal position to a second operative position. In the first insertion/withdrawal position (see FIGS. 1, 1A, 2 and 2A), distal end 104 of tubular body 102 is at a distal most position such that longitudinal ribs 112 of onion sleeve portion 108 lie flush with the outer surface of tubular body 102. Meanwhile, in the operative position (see FIGS. 1B, 3 and 3A), distal end 104 of tubular body 102 is at a proximal most position wherein longitudinal ribs 112 of onion sleeve portion 108 extend radially outward from tubular body 102.

Apparatus 100 desirably further includes a hollow inner tube 120 received within and extending through tubular body 102, an onion sleeve portion trigger 122 and an onion sleeve portion slider 124 each slidably disposed on tubular body 102. In the embodiments shown, the inner tube 120 is provided with a threaded distal end 126. Threaded distal end 126 threadably receives a back-up ring 128 thereon. Back-up ring 128 acts to abut the distal end of tubular body 102 in a manner such that inner tube 120 is prevented from being proximally withdrawn from tubular body 102.

As seen in FIG. 1, trigger 122 preferably includes a cylindrical body portion 130 defining a lumen 132 therethrough and a pair of handles 134 extending radially therefrom. Trigger 122 includes a locking screw 136 oriented to extend through body portion 130 of trigger 122 and to engage the outer surface of tubular body 102. In use, tightening of locking screw 136 will secure trigger 122 against tubular body 102 and prevent axial movement of trigger 122 along tubular body 102. In the embodiment shown, trigger 122 is coupled to inner tube 120 such that axial reciprocal movement of trigger 122 along tubular body 102 will cause inner tube 120 to reciprocally slide within tubular body 102.

Slider 124 includes an annular collar 138 having a flange 140 extending therefrom and a locking screw 142 oriented to extend through annular collar 138 and to engage the outer surface of tubular body 102. In use, tightening of locking screw 142 will secure slider 124 against tubular body 102 and prevent axial movement of slider 124 along tubular body 102.

Apparatus 100 further includes a firing assembly 144 operatively connected to a proximal end of inner tube 120.

Figure 5:
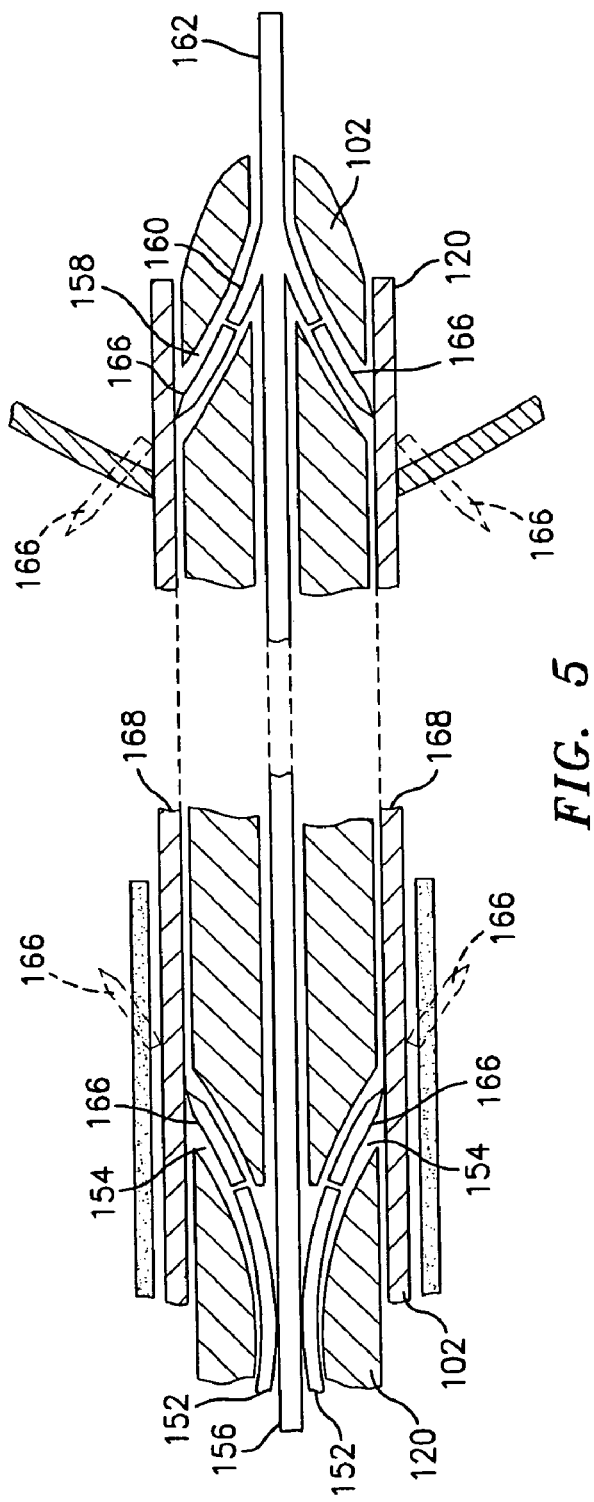
FIG. 5 is a cross-sectional view of the distal end of the apparatus of FIG. 1, taken along a longitudinal axis thereof.
Figure 6:
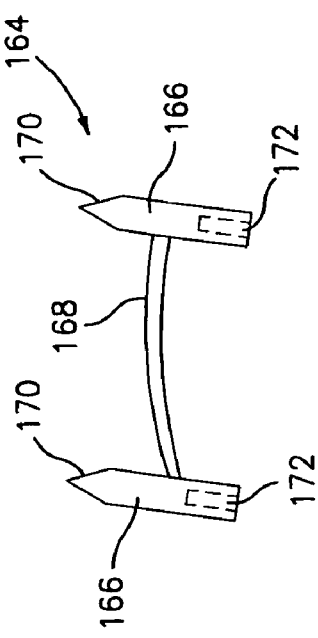
FIG. 6 is a side elevational view of a needle suture assembly in accordance with the present disclosure.

Firing assembly 144 includes a central body portion 146 having a proximal needle driver knob 148 and a distal needle driver knob 150 threadingly coupled thereto. As seen in FIG. 5, firing assembly 144 further includes a plurality of peripheral firing rods 152 extending through inner tube 120, between proximal needle driver knob 148 and a corresponding plurality of radially oriented suture needle passages 154 formed near a distal end of inner tube 120. In accordance with the present disclosure, suture needle passages 154 are distally oriented and are radially aligned with slots 110 of tubular body 102.

Firing assembly 144 additionally includes a central firing rod 156 extending through inner tube 120, between distal needle driver knob 150 and a plurality of radially oriented suture needle passages 158 formed near a distal end of inner tube 120. Preferably, suture needle passages 158 are formed distally of needle passages 154, are oriented in a proximal direction and are radially aligned with slots 110 of tubular body 102. Central firing rod 156 includes a plurality of proximally oriented prongs 160 configured and adapted to be received within needle passages 158.

In one embodiment, central firing rod 156 includes a distal tip 162 which extends through the distal end of inner tube 120. Distal tip 162 acts like a guide wire and aides the surgeon in guiding and inserting apparatus 100 through the urethra of the patient.

Apparatus 100 further includes needle assembly 164 (see FIG. 6) having a pair of needles 166 interconnected by a suture tether 168. Preferably, each needle 166 includes a sharpened end 170 and a recess 172 formed in the opposite end thereof. In accordance with the present disclosure, needle assembly 164 is coupled to apparatus 100 such that a first needle 166 is positioned in needle passage 158 and a second needle 166 is positioned in needle passage 154, wherein each needle 166 is oriented with sharpened end 170 oriented radially outward. Accordingly, recess 172 of each needle 166 is configured and adapted to be seated on the distal ends of firing rods 152, 156. In accordance with the present disclosure, suture tether 168 extends from a first needle 166, out through needle passage 154, along the outer surface of inner tube 120, into needle passage 158 and to a second needle 166.

In accordance with the present disclosure, it is preferred that five needle assemblies 164 be operatively received within a corresponding number of respective needle passages 154 and 158. While a set of five needle assemblies 164 is preferred, it is envisioned that any number of needle assemblies 164 can be used. It is contemplated that needles 166 of needle assemblies 164 can be made from any surgical grade material, such as stainless steel or titanium, however, it is envisioned that needles 166 are preferably made from a medical grade bio-absorbable material, such as, for example, polyglycolic acid (PGA) and/or polylactic acid (PLA). It is further envisioned that suture tether 168 of needle assembly 164 also be made of a suitable bio-absorbable material.

A preferred method of use and operation of anastomosis apparatus 100 in performing a radical prostatectomy anastomosis will now be described in greater detail with reference to FIGS. 1-10 and in particular with reference to FIGS. 7-10. Apparatus 100 can be used in either the retropubic or the perineal prostatectomy approaches. With the prostate removed, the bladder neck "N" of the bladder "B" is first reconstructed by everting the inner mucosal lining of bladder "B" and suturing it down to the outer wall of bladder "B", using known surgical techniques. Likewise, urethral stump "S" of urethra "U" is reconstructed by everting the inner mucosal lining of urethral stump "S" and suturing it down to the outer wall of urethra "U", using known surgical techniques.

Preferably, with bladder neck "N" reconstructed, bladder neck "N" is sized to properly accommodate and retain bladder fitting 104 within bladder "B" using a standard tennis racket type closure (i.e., the opening of the bladder neck constituting the head of the tennis racket and a radial incision extending from the bladder neck constituting the handle portion of the tennis racket. Most preferably, bladder neck "N" is sized to be approximately 7-8 mm in diameter.

Figure 7:
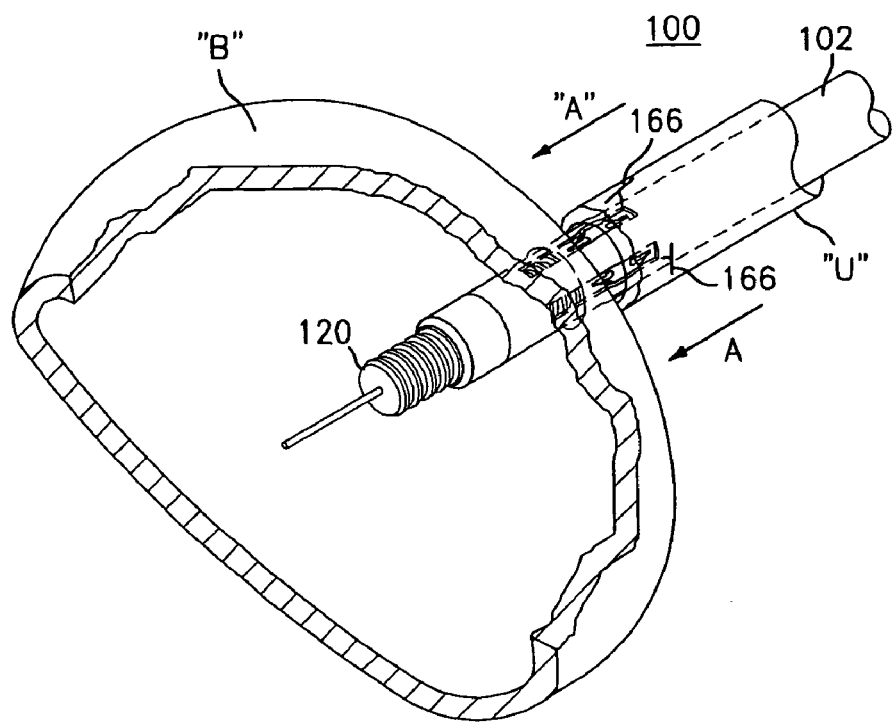
FIG. 7 is a partial cross-sectional view of a portion of a urinary system of a patient with a distal end of the apparatus of FIG. 1 deployed therein with the radially deformable onion sleeve in the retracted configuration.
Figure 8:
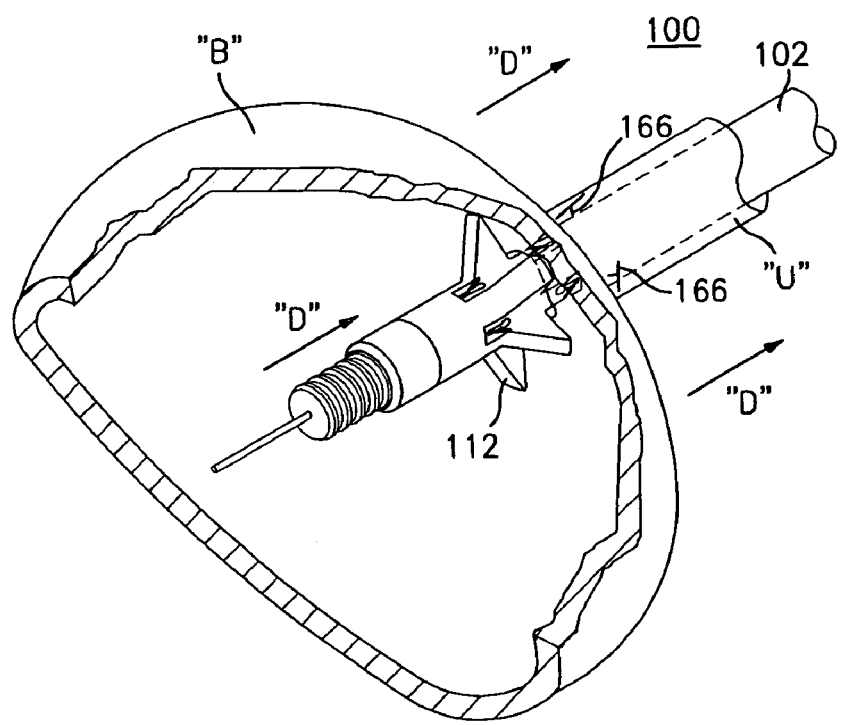
FIG. 8 is a partial cross-sectional view of a portion of the urinary system with the distal end of the apparatus of FIG. 1 deployed therein with the radially deformable onion sleeve of the expanded and positioned to draw the bladder into apposition with the urethral stump.
Figure 9:
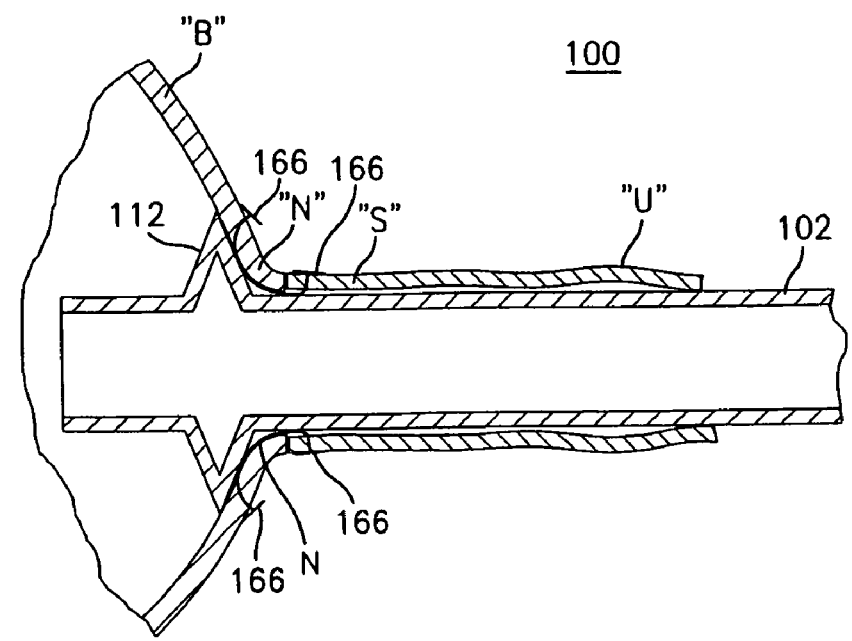
FIG. 9 is a cross-sectional view of a portion of the urinary system with the apparatus of FIG. 1 deployed therein and the radially deformable onion sleeve expanded and tissue anchors deployed into the bladder and the urethral stump.

With bladder neck "N" reconstructed, apparatus 100 is passed trans-urethrally through urethra "U" until distal end 104 of tubular body 102 extends out of urethral stump "S", as indicated by arrow "A" in FIG. 7. In particular, distal end 104 of tubular body 102 is positioned such that the distal end of urethral stump "S" is positioned distally of needle passages 154.

With apparatus 100 so positioned, proximal needle driver knob 148 is rotated about central body portion 146. The rotation of driver knob 148 results in the distal advancement of peripheral firing rods 152 through inner tube 120. As such, proximal needles 166 are radially ejected out through suture needle passages 154 and into urethral stump "S", as seen FIG. 7. Driver knob 148 is advanced until proximal needles 166 completely pass through urethral stump "S" at which time driver knob 148 is rotated in an opposite direction in order to withdraw peripheral firing rods 152 back into inner tube 120.

Next, apparatus 100 is further advanced distally until distal end 104 of tubular body 102 enters bladder neck "N" of bladder "B". In accordance with the present disclosure, apparatus 100 is distally advanced into bladder "B" until onion sleeve portion 108 of tubular body 102 is positioned distally of bladder neck "N". With apparatus 100 so positioned, onion sleeve portion 108 of tubular body 102 is deployed. In accordance with the present disclosure, onion sleeve portion 108 is deployed by locking slider 124 in place against tubular body 102, holding slider 124 and advancing trigger 122 in a proximal direction relative to slider 124, i.e., in a direction indicated by arrow "C" of FIGS. 4A and 4B. Accordingly, proximal movement of trigger 122 relative to slider 124 results in the proximal movement of inner tube 120 through tubular body 102. Since back-up ring 128 is secured to the distal end of inner tube 120, proximal advancement of inner tube 120 through tubular body 102 results in back-up ring 128 pressing against the distal end of tubular body 102 thereby causing onion sleeve portion 108 to compress. Compression of onion sleeve portion 108 results in the deflection of ribs 112 along fold lines 114A and 114B and thus in turn the radially expansion of onion sleeve portion 108.

With onion sleeve portion 108 in the deployed position, trigger 122 is secured in place along tubular body 102 by tightening locking screw 136. Next, apparatus 100 is drawn in a proximal direction, as indicated by arrow "D" in FIG. 8, through urethra "U". In so doing, ribs 112 of expanded onion sleeve portion 108 contact the inner surface of bladder "B" and act as an anchor to aid in the proximal drawing of bladder "B" until bladder neck "N" contacts urethral stump "S".

With bladder "B" contacting urethral stump "S", distal needle driver knob 150 is rotated about central body portion 146. The rotation of driver knob 150 results in the proximal advancement of central firing rod 156 through inner tube 120. As such, prongs 160 of central firing rod 156 press against needles 166 in order to radially eject needles 166 out through suture needle passages 158 and into bladder neck "N" (see FIG. 9). Driver knob 150 is advanced until distal needles 166 completely pass through bladder neck "N" at which time driver knob 50 is rotated in an opposite direction in order to withdraw prongs 160 of central firing rod 156 back in to inner tube 120.

Figure 4A:
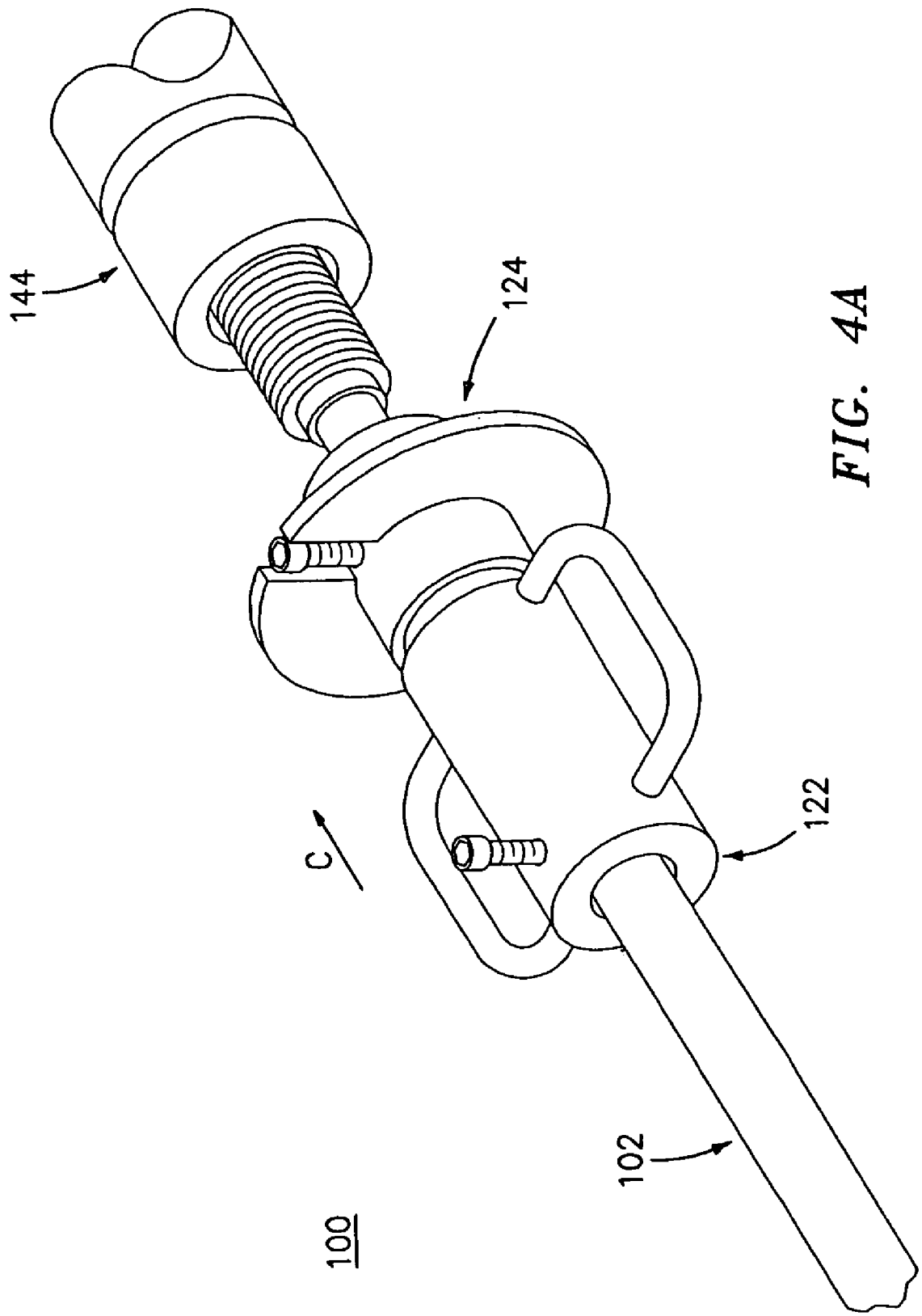
FIG. 4A is an enlarged perspective view of an engineering model of a proximal end of the apparatus of FIG. 1A, while in the retracted position.
Figure 4B:
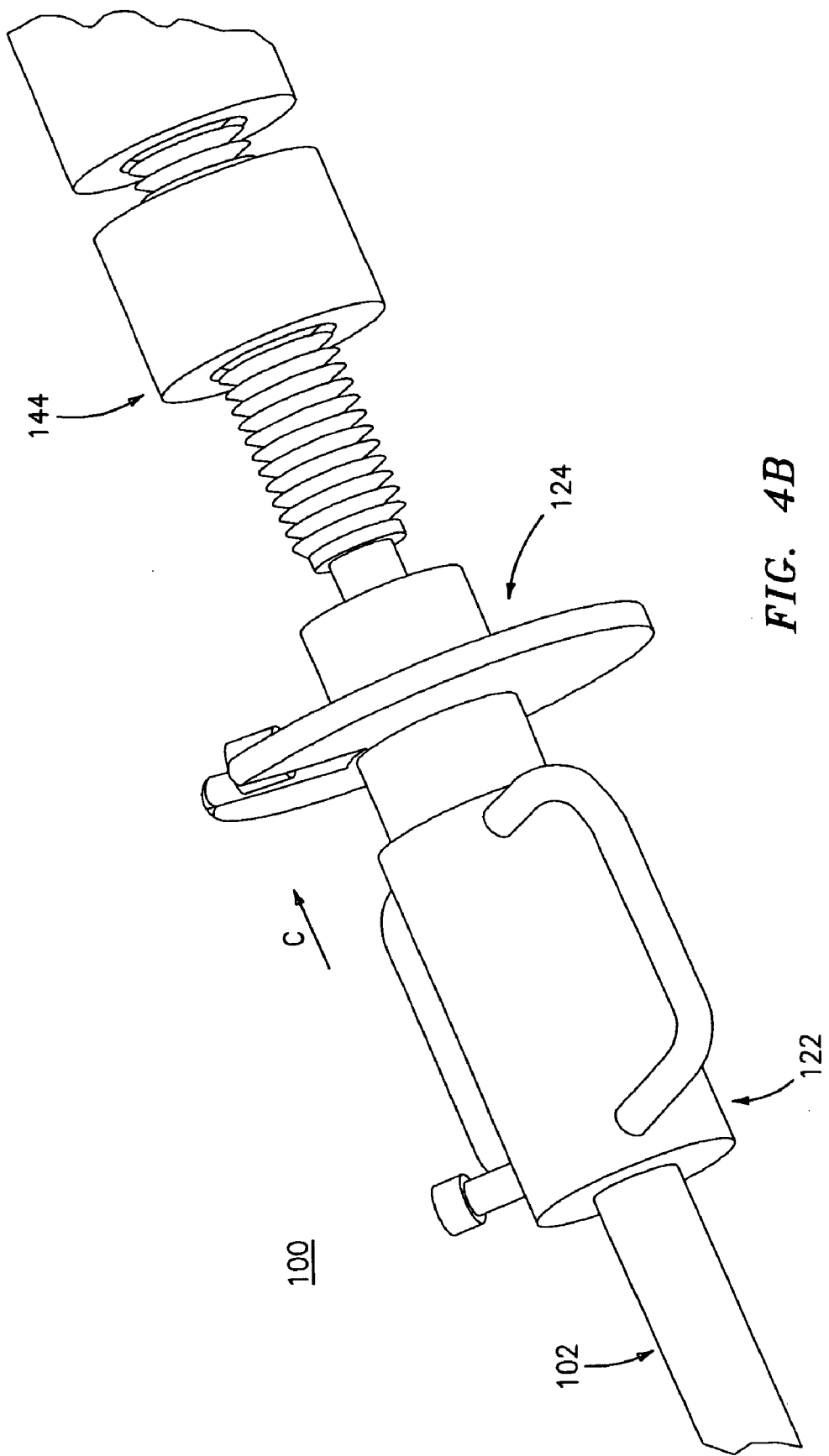
FIG. 4B is an enlarged perspective view of an engineering model of a proximal end of the apparatus of FIG. 1B, while in the deployed position.
Figure 10:
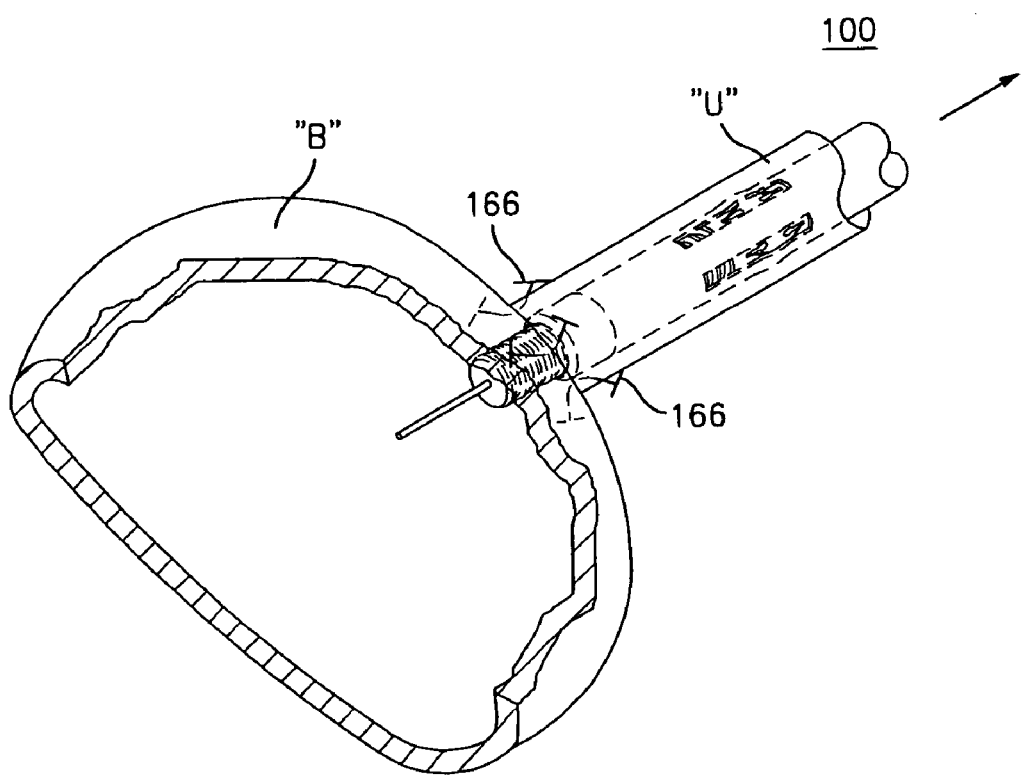
FIG. 10 is a partial cross-sectional view of a portion of the urinary system with the apparatus of FIG. 1 being withdrawn through the urethra

Next, onion sleeve portion 108 is returned to the insertion position, in the present instance the withdrawal position, by loosening locking screw 136 of trigger 122 and proximally advancing trigger 122 (i.e., in a direction opposite to direction "C" as seen in FIGS. 4A and 4B). In so doing, ribs 112 of onion sleeve portion 108 retract to lie flush with the outer surface of tubular body 102. With onion sleeve portion 108 returned to the insertion/withdrawal position, the surgeon withdraws apparatus 100 proximally through urethra "U", as seen in FIG. 10.

While the apparatus in accordance with the present disclosure has been described as being used in connection with a radical prostatectomy, it is envisioned that apparatus having a similar structure and mode of operation can be used in various other surgical procedures. The methods and apparatus disclosed herein may be used for approximating and/or joining the urethra and bladder, intestinal portions of the body, blood vessels or any other body vessels. It will be understood that various modifications may be made to the embodiments of the presently disclosed anastomosis device and method disclosed herein. For example, an alternative mode of operation is envisioned in which apparatus 100 is advanced distally through urethra "U" and into bladder "B", onion sleeve portion 108 is deployed, apparatus 100 is retracted in order to approximate bladder neck "N" with urethral stump "S", firing knobs 148 and 150 are sequentially fired in order to eject needles 166 of needle assembly 164 into bladder neck "N" and urethral stump "S", respectively, onion sleeve portion 108 is retracted and apparatus 100 is withdrawn from urethra "U".

The expandable anchor for engaging a first and/or second body vessel may comprise any expandable structure, including those disclosed in certain embodiments of the following PCT Applications, all filed on an even date herewith: application entitled Method And Apparatus For Anastomosis Including An Anchoring Sleeve, invented by Scott Manzo; Method And Apparatus For Anastomosis Including An Anchor For Engaging A Body Vessel And Deployable Sutures, invented by Scott Manzo; Method And Apparatus For Anastomosis Including Annular Joining Member, invented by Scott Manzo; Method And Apparatus For Anastomosis Including Annular Joining Member, invented by Scott Manzo; Method And Apparatus For Anastomosis Including An Expandable Member, invented by Russell Heinrich and Scott Manzo; Method And Apparatus For Anastomosis Including An Expandable Anchor, invented by Russell Heinrich and Scott Manzo; the disclosures of which are all hereby incorporated by reference herein, in their entirety.

The joining member for joining a first and/or second body vessel may comprise any joining member, including those disclosed in certain embodiments of the following PCT Applications, all filed on an even date herewith: application entitled Method And Apparatus For Anastomosis Including An Anchoring Sleeve, invented by Scott Manzo; Method And Apparatus For Anastomosis Including An Anchor For Engaging A Body Vessel And Deployable Sutures, invented by Scott Manzo; Method And Apparatus For Anastomosis Including An Anchor For Engaging A Body Vessel And Deployable Sutures, invented by Scott Manzo; Method And Apparatus For Anastomosis Including An Anchoring Sleeve, invented by Scott Manzo; Method And Apparatus For Anastomosis Including Annular Joining Member, invented by Scott Manzo; Method And Apparatus For Anastomosis Including Annular Joining Member, invented by Scott Manzo; Method And Apparatus For Anastomosis Including An Expandable Member, invented by Russell Heinrich and Scott Manzo; Method And Apparatus For Anastomosis Including An Expandable Anchor, invented by Russell Heinrich and Scott Manzo; the disclosures of which are all hereby incorporated by reference herein, in their entirety.

Therefore, the above description should not be construed as limiting, but merely as an exemplification of a preferred embodiment. For example, the locking screws may be replaced with a latch or any other structure for locking the positions of the inner tube and tubular body with respect to one another. In addition, the firing rods may be moved by an activator that also moves in a proximal distal direction. The firing rods may also include separate firing rods for the proximal and distal needles. Those skilled in the art will envision other modifications within the scope of the present disclosure.

What is claimed is:

1. An apparatus for joining a first body vessel and a second body vessel, comprising:
   a) a tubular body having a proximal end, a distal end and an onion portion integral to the tubular body, formed near the distal end of the tubular body, and configured for engaging the first body vessel, the onion portion having a first position and a second position extending outside a radial dimension of the tubular body;
   b) an inner tube disposed within the tubular body and at least partially within the onion portion, the inner tube being slidably movable to deploy the onion portion from the first position to the second position, the inner tube defining a plurality of passages;
   c) a plurality of needles, each needle being disposed in one of the plurality of passages; and
   d) a firing assembly for deploying the needles from the passages, the firing assembly including a first firing mechanism configured for distal movement to deploy at least one of the needles in a distal direction, and a second firing mechanism configured for proximal movement to deploy at least one of the needles in a proximal direction.

2. The apparatus of claim 1, wherein the passages comprise at least one pair of passages formed below the onion portion, including a proximal and a distal passage.

3. The apparatus of claim 2, wherein the needles comprise at least one needle assembly disposed within the at least one pair of passages, each needle assembly including a pair of needles connected by a suture.

4. The apparatus of claim 3, wherein the at least one needle assembly is arranged so that a first needle is disposed in the proximal passage and a second needle is disposed in the distal passage.

5. The apparatus of claim 1, wherein the firing assembly includes a plurality of rods, each of the plurality of rods being operatively coupled to at least one of the needles.

6. The apparatus of claim 5, wherein the firing assembly comprises a first knob operatively coupled with at least one first rod, the at least one rod being operatively coupled with the first needle of the at least one needle assembly.

7. The apparatus of claim 6, wherein the firing assembly comprises a second knob operatively coupled with at least one second rod, the at least one rod being operatively coupled with the second needle of the at least one needle assembly.

8. The apparatus of claim 7, wherein distal advancement of the at least one first rod deploys the first needle and proximal advancement of the at least one second rod deploys the second needle.

9. An apparatus for joining a first body vessel and a second body vessel, comprising:
   a) a tubular body having a proximal end, a distal end and an onion portion formed near the distal end of the tubular body, the onion portion having a first position and a second position extending outside a radial dimension of the tubular body, the onion portion configured for engaging the first body vessel when in the second position thereof;
   b) an inner tube disposed within the tubular body and being slidably movable to deploy the onion portion from the first position to the second position, the inner tube defining a plurality of passages;
   c) a plurality of needles, each needle being disposed in one of the plurality of passages such tat a sharpened end of each needle is oriented radially outward; and
   d) a firing assembly for deploying the needles from the passages, the firing assembly including a first firing mechanism configured for distal movement to deploy at least one of the needles in a distal direction, and a second firing mechanism configured for proximal movement to deploy at least one of the needles in a proximal direction.

10. The apparatus of claim 9, wherein the passages comprise at least one pair of channels formed radially inward of the onion portion, each channel including a proximal and a distal segment.

11. The apparatus of claim 10, wherein the proximal segment and the distal segment of each channel are oriented toward one another.

12. An apparatus for joining a first body vessel and a second body vessel, comprising:
   a) a tubular body having a proximal end, a distal end and an onion portion formed near the distal end of the tubular body, the onion portion having a first position and a second position extending outside a radial dimension of the tubular body, the onion portion configured for engaging the first body vessel when in the second position thereof;
   b) an inner tube disposed within the tubular body and being slidably movable to deploy the onion portion from the first position to the second position, the inner tube defining a plurality of passages;
   c) a tissue anchor comprising a pair of needles interconnected by a suture tether, each of the pair of needles being disposed in one of the plurality of passages; and
   d) a firing assembly for ejecting the tissue anchor from the apparatus for implantation of one of the pair of needles into a respective one of the first and second body vessels, the firing assembly including a distal tip extending through a distal end of the inner tube.

13. The apparatus of claim 12, wherein the pair of needles and the suture tether are made from a medical grade bio-absorbable material.

14. The apparatus of claim 13, wherein the medical grade bio-absorbable material is selected from the group consisting of polyglycolic acid and polylactic acid.

* * * * *